(12) United States Patent
Nilforushan et al.

(10) Patent No.: US 8,876,875 B1
(45) Date of Patent: Nov. 4, 2014

(54) THERMAL THERAPY APPAREL

(71) Applicant: Snapbac, LLC, Escondido, CA (US)

(72) Inventors: Ali Nilforushan, Encinitas, CA (US); Kevin Bello, Escondido, CA (US)

(73) Assignee: Snapbac, LLC, Escondido, CA (US)

( * ) Notice: Subject to any disclaimer, the term of this patent is extended or adjusted under 35 U.S.C. 154(b) by 0 days.

(21) Appl. No.: 14/186,269

(22) Filed: Feb. 21, 2014

(51) Int. Cl.
*A61F 7/00* (2006.01)
*A41D 13/00* (2006.01)
*A41D 27/20* (2006.01)
*A61F 7/02* (2006.01)

(52) U.S. Cl.
CPC ........................................ *A61F 7/02* (2013.01)
USPC .................. 607/108; 607/96; 607/114; 2/69; 2/247

(58) Field of Classification Search
CPC ............. A41D 1/00; A41D 1/02; A41D 1/04; A41D 27/20; A61F 7/00; A61F 7/02; A61F 7/08; A61F 7/086; A61F 2007/00; A61F 2007/02; A61F 2007/023; A61F 2007/0231; A61F 2007/0233; A61F 2007/0234; A61F 2007/0238
USPC .................. 601/1, 15; 607/96, 114, 108–112; 2/2.16, 69, 171.2, 247
See application file for complete search history.

(56) References Cited

U.S. PATENT DOCUMENTS

| | | | | |
|---|---|---|---|---|
| 2,632,894 A * | 3/1953 | Louis | ............................... | 2/320 |
| 3,263,292 A * | 8/1966 | Fekete | ......................... | 24/595.1 |
| 3,266,113 A * | 8/1966 | Flanagan, Jr. | .................. | 24/452 |
| 3,708,837 A * | 1/1973 | Chiba | .............................. | 24/450 |
| 4,676,247 A * | 6/1987 | Van Cleve | ..................... | 607/112 |
| 5,038,779 A * | 8/1991 | Barry et al. | .................... | 607/108 |
| 5,179,944 A * | 1/1993 | McSymytz | ................... | 607/114 |
| 5,230,333 A * | 7/1993 | Yates et al. | ..................... | 607/111 |
| 5,269,023 A * | 12/1993 | Ross | ................................. | 2/66 |
| 5,466,251 A * | 11/1995 | Brunson et al. | ................ | 607/112 |
| 5,534,021 A * | 7/1996 | Dvoretzky et al. | ........... | 607/112 |
| 5,605,144 A * | 2/1997 | Simmons et al. | ............. | 126/204 |
| 5,761,775 A * | 6/1998 | Legome et al. | ................. | 24/450 |
| 5,826,273 A * | 10/1998 | Eckes | ................................ | 2/69 |
| 5,855,023 A * | 1/1999 | Clingenpeel et al. | ................. | 2/7 |
| 5,930,876 A * | 8/1999 | Takizawa et al. | ............... | 24/452 |
| 6,185,744 B1 * | 2/2001 | Poholski | .......................... | 2/102 |
| 6,656,210 B1 * | 12/2003 | Plewes | ......................... | 607/112 |
| 7,739,748 B2 | 6/2010 | Nilforushan et al. | | |
| 8,220,074 B2 * | 7/2012 | Sutker | ................................ | 2/69 |
| 8,256,034 B2 * | 9/2012 | Berner et al. | ..................... | 2/455 |

(Continued)

*Primary Examiner* — Justine Yu
*Assistant Examiner* — Christopher Miller
(74) *Attorney, Agent, or Firm* — Nicholas Pfeifer; Anton J. Hopen; Smith & Hopen, P.A.

(57) ABSTRACT

The present invention is a two-layer garment adapted to receive one or more body parts to provide a user with compression and thermal therapy. The two layers comprise of an inner base layer having a compression fit and an outer mesh layer. The layers are attached to one another such that an intermediate space exists between the two layers. The intermediate space is accessible through one or more openings to the intermediate space. The opening and intermediate space are adapted to receive a thermal transferring element. A thermal pouch having a plurality of projections on an outward facing surface may receive the thermal transferring element prior to insertion into the intermediate space or the projections may be located on the thermal transferring element itself. The outer mesh layer receives the projections securing the thermal transferring element at any location, resulting in unmatched customizable thermal and compression therapy.

18 Claims, 10 Drawing Sheets

(56) References Cited

U.S. PATENT DOCUMENTS

| | | | |
|---|---|---|---|
| 8,434,163 B1* | 5/2013 | Nudo | 2/102 |
| 2002/0052569 A1* | 5/2002 | Horning | 602/41 |
| 2004/0055076 A1* | 3/2004 | Yoo | 2/338 |
| 2005/0066406 A1* | 3/2005 | Sleesen | 2/69 |
| 2006/0213156 A1* | 9/2006 | Nilfuroshan | 54/79.1 |
| 2007/0106356 A1* | 5/2007 | Carstens | 607/112 |
| 2008/0125842 A1* | 5/2008 | Petitt | 607/108 |
| 2008/0201818 A1* | 8/2008 | Nilforushan et al. | 2/69 |
| 2009/0099488 A1* | 4/2009 | Hedberg | 601/5 |
| 2010/0152823 A1* | 6/2010 | Muchowicz | 607/112 |
| 2012/0165909 A1* | 6/2012 | Koudelka | 607/112 |
| 2013/0167332 A1* | 7/2013 | Terada et al. | 24/450 |

\* cited by examiner

THERMAL THERAPY APPAREL

BACKGROUND OF THE INVENTION

1. Field of the Invention

This invention relates, generally, to garments. More specifically, it relates to compression and thermal therapy garments.

2. Brief Description of the Prior Art

The art of heating and cooling the human body for prevention and/or treatment of injuries is well known and frequently practiced. Such treatments can not only relieve pain and increase flexibility, but can also alter the body's core temperature improving the ability to function properly. The state of the art has progressed greatly from manually holding bags of ice and warm towels to specialized wrapping devices containing hot/cold packs. These hot/cold packs are generically referred herein as thermal transferring elements (TFE's).

There currently exist numerous methods for applying and securing TFE's. One such method is manually holding a TFE, which has clear downsides, such as lacking of ability to secure in a hard to reach location and restricting the use of at least one hand. Another method is attaching a TFE to a body part using straps, wraps, adhesives, or other means. This option also accompanies several disadvantages. One disadvantage is the potential restriction of mobility in commonly treated body parts, such as a knee of shoulder. Another is the difficulty in securing such a device to a hard to reach body part or to an arm. Arguably, the biggest disadvantage is the possibility of securing the strap or warps too tightly, potentially resulting in impeded blood flow and damage to underlying tissue and muscle.

Accordingly, what is needed is a more efficient thermal therapy device allowing a user to easily apply and secure a TFE to a desired treatment area. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a more effective and easy to use thermal therapy device that enables a user to target a specific treatment area is now met by a new, useful, and nonobvious invention.

The novel structure includes a garment having a base layer and an outer layer, where the base layer is adapted to receive one or more body parts and abuts the skin of the wearer. The outer layer comprises of mesh and is secured to the base layer such that an intermediate space is defined between the base layer and the outer layer. The intermediate space is capable of receiving a thermal transferring element through an opening to the intermediate space. The novel structure further includes a thermal pouch capable of receiving the thermal transferring element. The thermal pouch has an outward facing surface and an inward facing surface with the outward facing having a plurality of projections. The plurality of projections are generally equidistantly spaced and extend outwardly such that they are capable of being received by the holes in the mesh of the outer layer of the garment. Additionally, the inward facing surface is thermally transmissive.

In a certain embodiment, the novel structure lacks a thermal pouch. In this embodiment, the thermal transferring element has a first smooth side and a second side containing a plurality of projections. Similar to the thermal pouch, the plurality of projections on the thermal transferring element are generally equidistantly spaced and are adapted to be received by openings present in the outer mesh layer to secure the thermal transferring element in a desired location.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
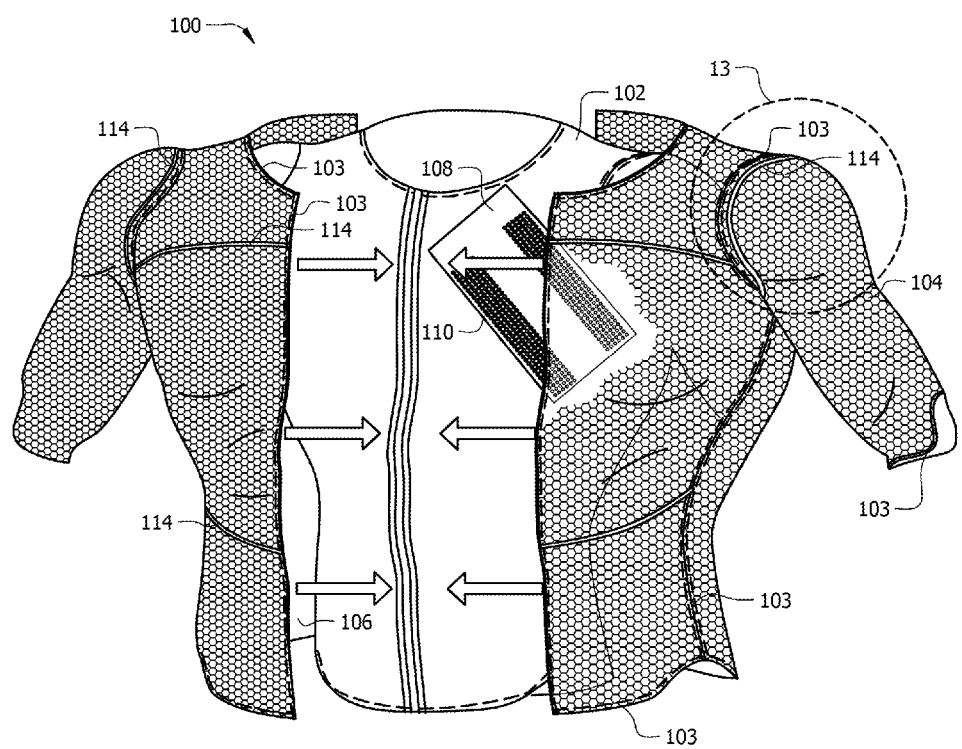
FIG. 1 is an exploded view of an embodiment of the present invention having a partial cutaway of the outer mesh layer to more clearly display the thermal pouch.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention is a two-layer garment, adapted to receive one or more body parts, for providing a user with compression and thermal therapy. The two layers comprise of an inner base layer having a compression fit and an outer mesh layer. The outer layer is secured to the base layer such that an intermediate space exists between the two layers. The layers are preferably secured to one another in such a manner that the intermediate space is compartmentalize. One or more openings are located, preferably in the outer layer, to allow for the insertion of a TFE into the intermediate space between the outer and inner layers of the garment. The inner base layer may contain the openings instead of or along with the outer layer. The opening may be slits or contain closures, such as a zipper.

The inner base layer is preferably thermally transmissive while also serving as a layer of protection between the TFE and the skin to prevent skin burn. In addition, the base layer is flexible enough to allow a user to move freely while also providing compressive properties to secure the garment to the user's body and to provide therapeutic compression. The outer layer may also comprise of flexible and compressive properties such that the TFE can be inserted into the intermediate space, but also be secured in a desired position by an inward (towards the body) compression force.

The compartments of intermediate space are preferably large, not only relative to the size of a corresponding TFE, but also to the size of the garment. For example, a shirt or jacket can have a space extending across the entire upper or lower back regions, or along the entire left and right front panels. Contemplated spaces can alternatively extend across the entire back or front (for pullovers) or even a single contiguous space across the entire back and front.

The TFE can have any suitable configuration, and can be enclosed or otherwise coupled to any sort of similarly configured thermal pouch. For example, the TFE can consist of a single gel pack, or multiple gel packs coupled at flex points. The TFE may be removably disposed in a thermal pouch. The thermal pouch has an outward facing surface (away from the body) and an inward facing surface (toward the body), and may contain a closure, such as a zipper or flap to temporarily secure the TFE inside the thermal pouch. The inward facing surface comprises a thin, thermally transmissive fabric, preferably being mesh with large holes to improve thermal transfer. The outward facing surface comprises of a thermally insulating fabric having a plurality of projections adapted to be received by the holes in the outer mesh layer of the garment. The engagement of the projections in the mesh, along with the compression force of the outer layer, secures the thermal pouch in place. In a certain embodiment, the projections are about 0.5 millimeters (mm) to about 3 mm tall and about 0.5 mm to about 3 mm in diameter. In a certain embodiment, the holes in the mesh outer layer are between about 0.5 mm and about 2 mm in diameter, but can extend to about 3 mm in diameter when the material is stretched. In another embodiment, the holes and projections may have another shape and size known to a person having ordinary skill in the art such that the holes may receive the projections.

In a certain embodiment, the TFE does not require a thermal pouch and contains a plurality of projections on the TFE itself. The plurality of projections is disposed on a predetermined side of the TFE intended to be the outward facing surface. Similar to the thermal pouch, the mesh of the garment's outer layer receives the projections on the TFE to secure the TFE in place. Such an embodiment allows the TFE to be easily cleaned and reapplied without having to worry about the cleanliness of the thermal pouch.

There are many advantages to the various embodiments of the present invention. One is the ability to adjustably secure a TFE to any body part covered by the garment in any desired orientation, so long as the projections, on the thermal pouch or on the TFE, are facing towards the outer mesh layer of the garment. Thus, a user may precisely and adjustably target any body part covered by the garment, instead of being limited to specific, unchangeable locations. Another advantage of the present invention is the ability to adjustably secure the TFE multiple times without weakening the strength of the engagement. Other systems, such as those using adhesive or hook and loop fasteners to secure the TFE to an article of clothing, do not have this advantage because the adhesive and hook and loop fasteners weaken after each attachment and removal.

An additional advantage of the present invention is the enablement of a user to apply a TFE to a hard to reach area, such as the back, without requiring the assistance of another. The user can simply secure the TFE to the hard to reach location before clothing him/herself with the garment. Moreover, the present invention enables a user to maintain the location of the TFE without occupying his/her hands. Accordingly, the user can engage in activities that require the use of one or both hands while receiving thermal and compression therapy. Furthermore, a user could apply multiple TFE's, simultaneously allowing for the use of cold and/or heat therapy to multiple treatment sites without requiring additional support to secure the TFE's to the user's body.

Arguably, the most advantageous aspect of the present invention is the ability to engage in athletic activity while one or more TFE's are secured to the body. An athlete wearing a garment of the present invention is able to keep body parts warm during periods of inactivity without having to remove the garment prior to resuming athletic activity. Allowing a user to wear the garment with a heated TFE during an athletic activity will keep his/her muscles warm to aid in preventing injury. Alternatively, an athlete can cool parts of the body during strenuous activity to prevent overheating. Additionally, the TFE provides additional padding to the body part receiving treatment, which could aid in preventing impact injuries to the already compromised body part. Finally, after the athletic activity, the garment can be used to treat sore muscles or injured body parts, such as a sprained ankle.

One of the features of the present invention that enables the abovementioned benefits is the compressive base layer and compressive nature of the outer mesh layer. The base layer of the garment snugly fits the body of the wearer and the outer mesh layer firmly presses the TFE against the user's body. The term "snug fit" means that the article of clothing is tight on the wearer's body, having little or no slack in the material. The term "presses," as used in this context, means exerting a force on the TFE towards the body of the user. The force on the TFE increases the efficiency of heat transfer by increasing the surface area of the TFE in contact with the body. Furthermore, pressure increases the compression force already supplied from the base layer of the garment, which aids in preventing swelling of an injured body part and can keep muscles in their proper physiological location.

EXAMPLES

In a certain embodiment of the present invention, generally denoted as reference numeral 100 and shown in the exploded view of FIG. 1, the present invention includes base layer 102, outer mesh layer 104, and intermediate space 106 formed between base layer 102 and outer layer 104. This embodiment comprises a front, a rear, and two arm compartments of intermediate space 106 defined by connection points 103 between the two layers. Openings 114 to intermediate space 106 are simply slits located in outer mesh layer 104 that are capable of receiving thermal pouch 108. Thermal pouch 108, located in the front compartment in a user-determined orientation, contains a plurality of projections 110 on the outward facing surface. Outer mesh layer 104 receives projections 110 and secures thermal pouch 108 at the desired location.

Figure 2:
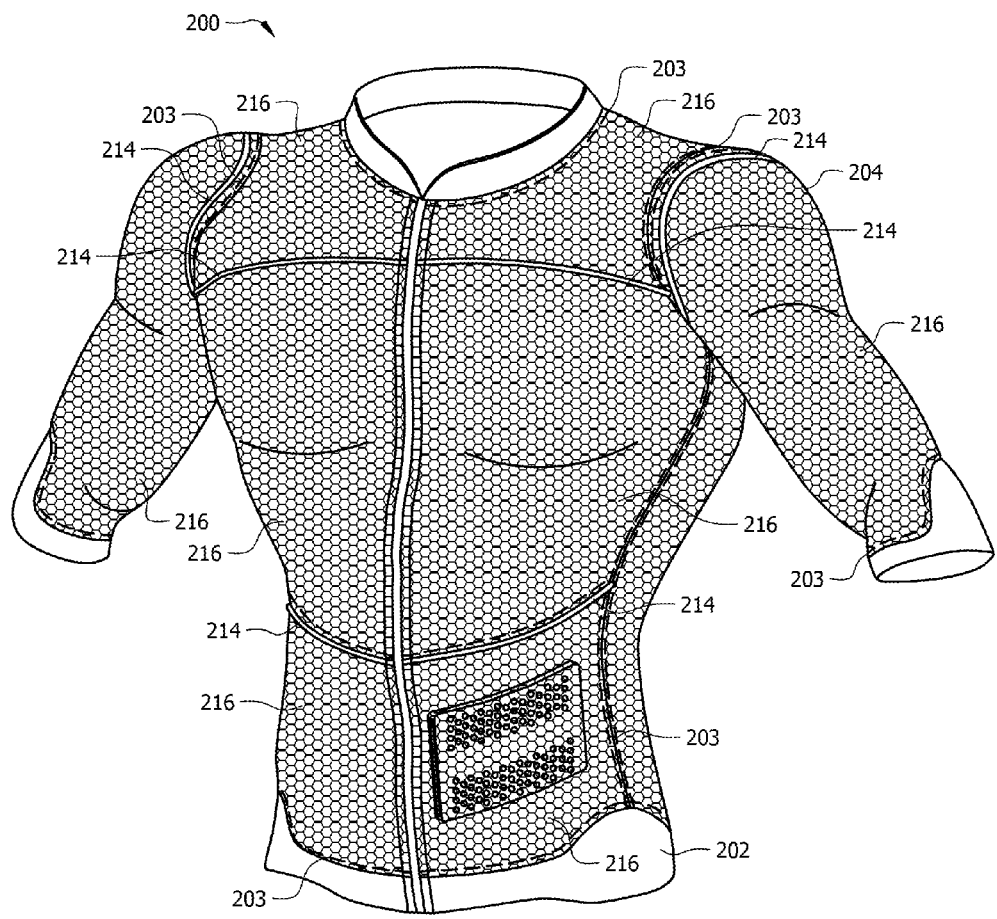
FIG. 2 is a perspective view of a certain embodiment of the present invention having a compartmentalized intermediate space.

As shown in FIG. 2, a certain embodiment of the present invention, generally denoted by reference numeral 200, includes additional compartments 216 in the intermediate space. The embodiment also includes additional connection points 203 between base layer 202 and outer mesh layer 204, which are located near openings 214. Comparable to embodiment 100, openings 214 are slits in outer mesh layer 204 that are capable of receiving the TFE or thermal pouch. In a certain embodiment, openings 214 may contain a closure mechanism and/or may be located at any position along outer mesh layer 204 or base layer 202 such that openings 214 allow access to intermediate space 206. The thermal pouch is shown in the user's bottom left front compartment.

Figure 3:
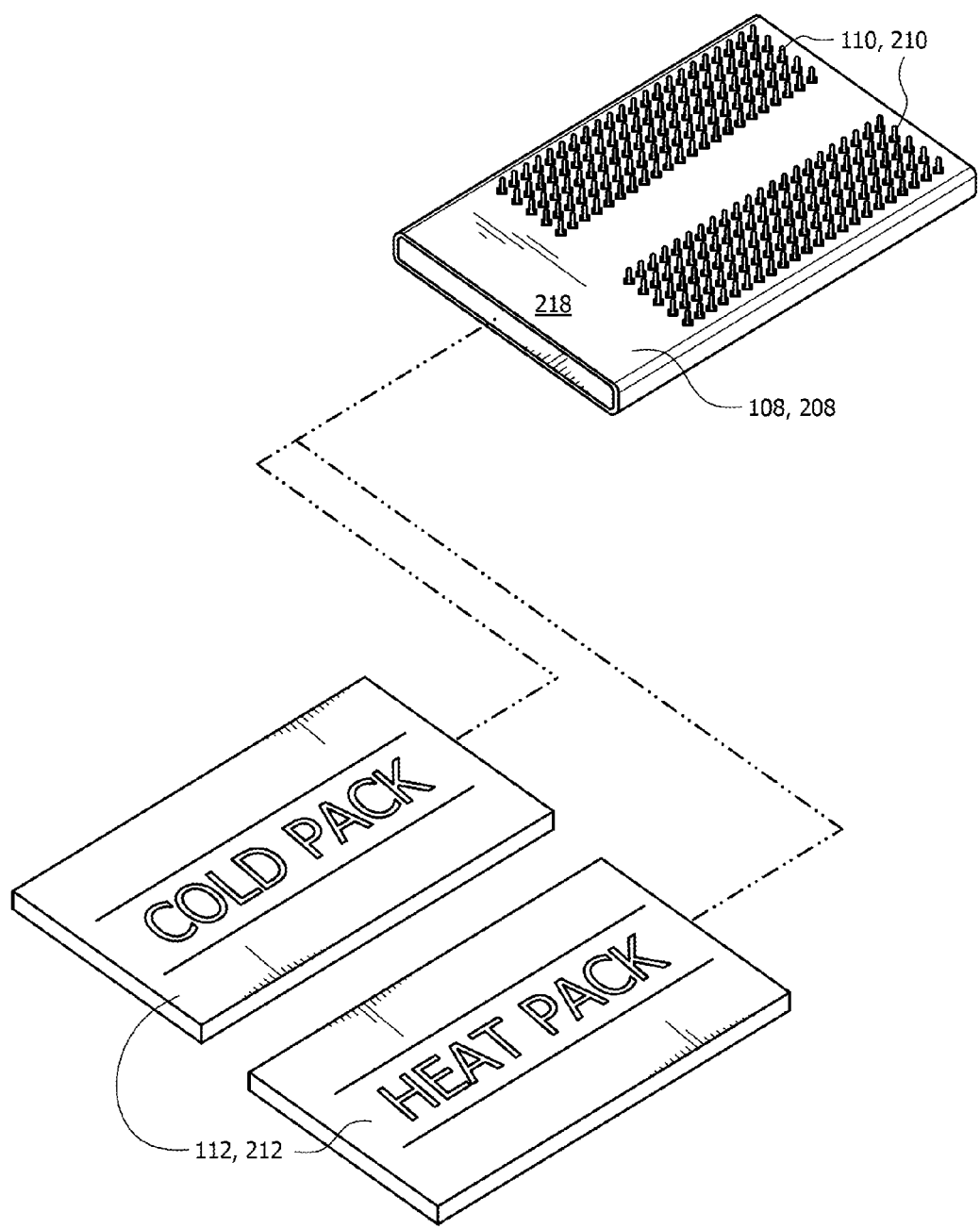
FIG. 3 is a perspective view illustrating the assembly of a certain embodiment of the thermal pouch and a certain embodiment of the thermal transferring elements.
Figure 4:
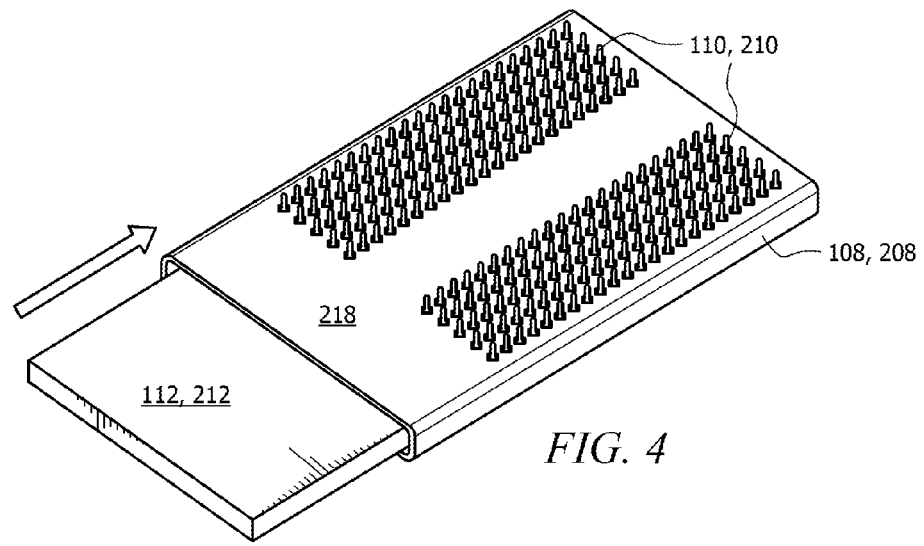
FIG. 4 depicts the insertion of a thermal transferring element into a thermal pouch.
Figure 5:
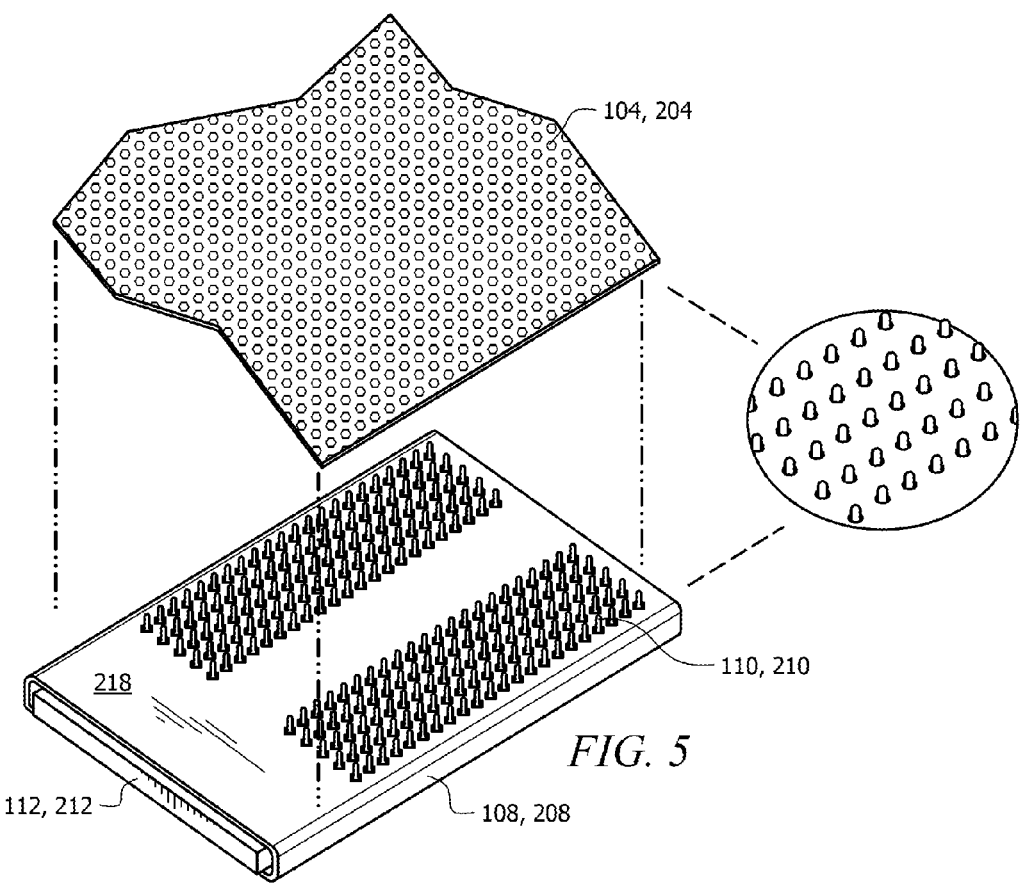
FIG. 5 illustrates a certain embodiment of the engagement between the projections on the thermal pouch and the outer mesh layer.

As shown in FIGS. 3-5, thermal pouch 108, 208 contains projections 110, 210 on outward facing surface 218 and is adapted to receive TFE 112, 212. Projections 110, 210 have a base affixed to the outward facing surface and a tip protruding therefrom such that the engagement of the projections and the mesh is between the base and tip of the projections (See FIG. 5). Moreover, projections 110, 210 may be arranged on outward facing surface 218 in any configuration known to a person having ordinary skill in the art such that the projections may be received with the holes in the outer mesh layer. Additionally, TFE 112, 212 may be capable of being both heated and cooled instead of having a TFE for cold and a TFE for heat. As shown specifically in FIG. 5 projections 110, 210 may be spaced in a manner such that the holes in outer mesh layer 104, 204 receive a single projection. In a certain embodiment, each hole in the outer mesh layer may receive more than one projection.

Figure 6:
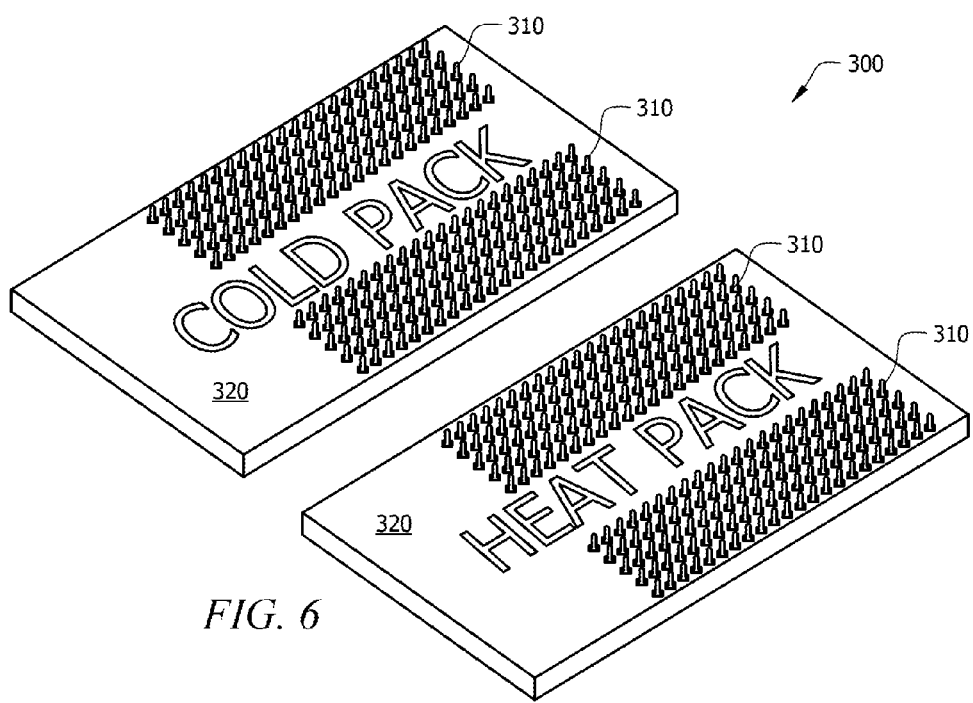
FIG. 6 depicts a certain embodiment of the thermal transferring element having projections on an outward facing surface.

As shown in FIG. 6, a certain embodiment the present invention may utilize a TFE, generally denoted by reference numeral 300, that includes plurality of projections 310 on outward facing surface 320 of TFE 300. TFE 300 is designed to be used without a thermal pouch. Similar to the thermal pouch, TFE 300 may have projections 310 arranged in any manner known to a person having ordinary skill in the art such that TFE 300 may be secured through the engagement of projections 310 with the holes of the outer mesh layer. Additionally, TFE 300 may be capable of being both heated and cooled instead of having a TFE for cold and a TFE for heat.

Figure 7:
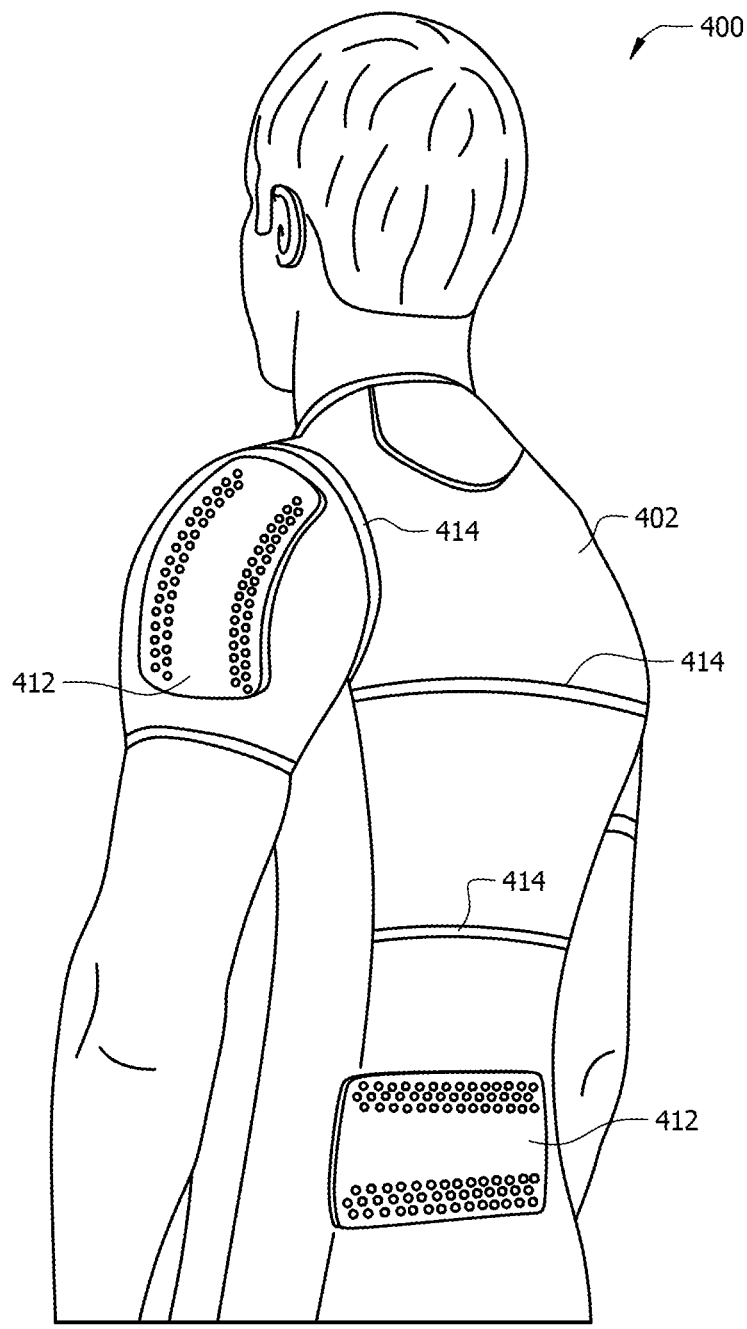
FIG. 7 is a rear perspective view of a certain embodiment of the present invention. The outer mesh layer is not visible in this figure only for clarity purposes.

As shown in FIG. 7, a certain embodiment of the present invention, generally denoted by reference numeral 400, may have openings 414 in base layer 402 capable of receiving TFE's 412 (alike to TFE 300 in FIG. 6) or thermal pouches, containing a TFE, such as the ones shown in FIGS. 1-5. Openings 414 may be positioned in base layer 402 at any location to provide one or more entrances to the intermediate space or compartments in the intermediate space. Note that the outer mesh layer is not visible in the figure only for illustration purposes.

Figure 8:
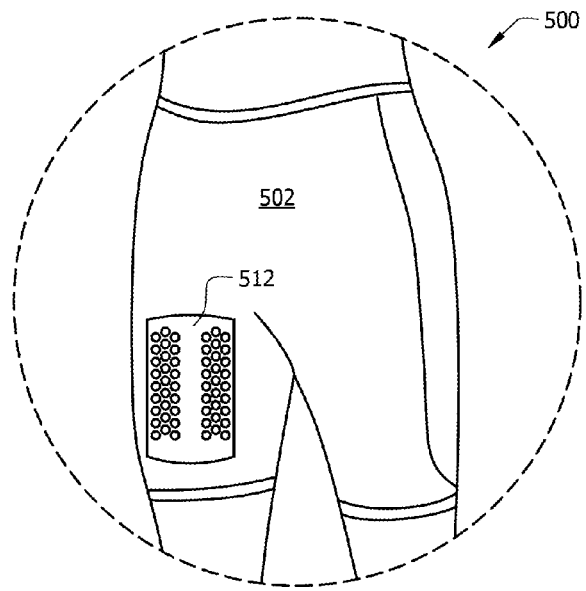
FIG. 8 is a front perspective view of a certain embodiment of the present invention. The outer mesh layer is not visible in this figure from clarity purposes.
Figure 9:
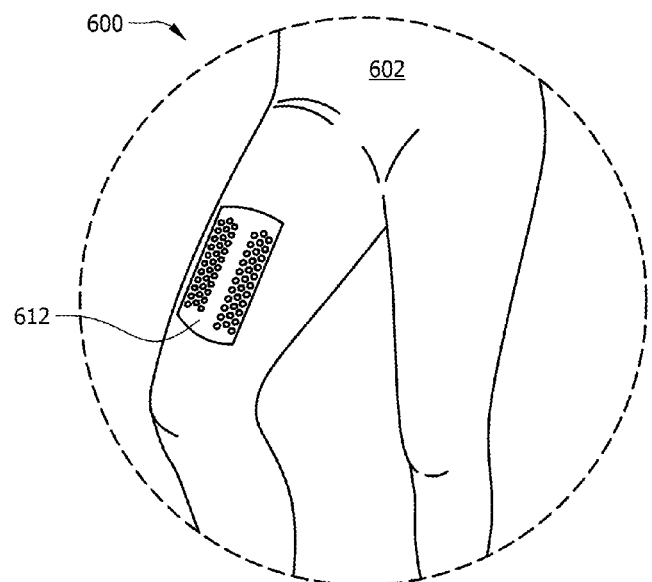
FIG. 9 is a front perspective view of a certain embodiment of the present invention. The outer mesh layer is not visible in this figure only for clarity purposes.

As shown in FIGS. 8 and 9, certain embodiments the present invention, generally denoted by reference numerals 500 and 600 respectfully, may be in any form capable of receiving one or more body parts. The outer mesh layer is not visible in the figures only for lucidity purposes. Both Figures illustrate base layer 502, 602 with TFE 512, 612 of embodiments 500, 600, respectfully. TFE 512, 612 is similar to TFE 300 in FIG. 6, but the embodiments may utilize a thermal pouch and TFE similar to those shown in FIGS. 1-5.

Figures 10, 11, 12:
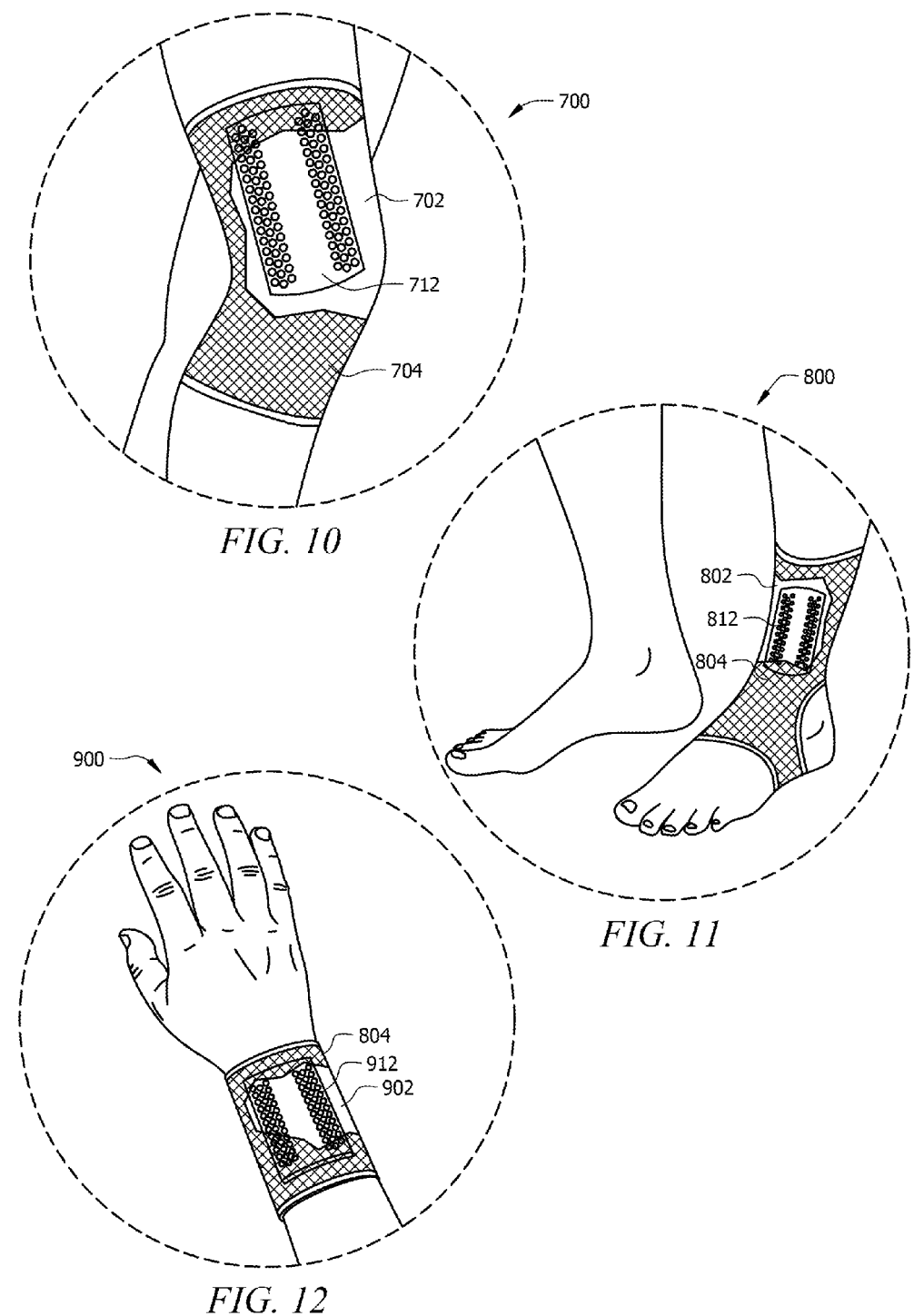
FIG. 10 is a side perspective view of a certain embodiment of the present invention. The figure utilizes a cutaway to aid in viewing the thermal transferring element.
FIG. 11 is a side perspective view of a certain embodiment of the present invention. The figure contains a cutaway to aid in viewing the thermal transferring element.
FIG. 12 is a top perspective view of a certain embodiment of the present invention. The figure contains a cutaway to aid in viewing the thermal transferring element.
Figure 13:
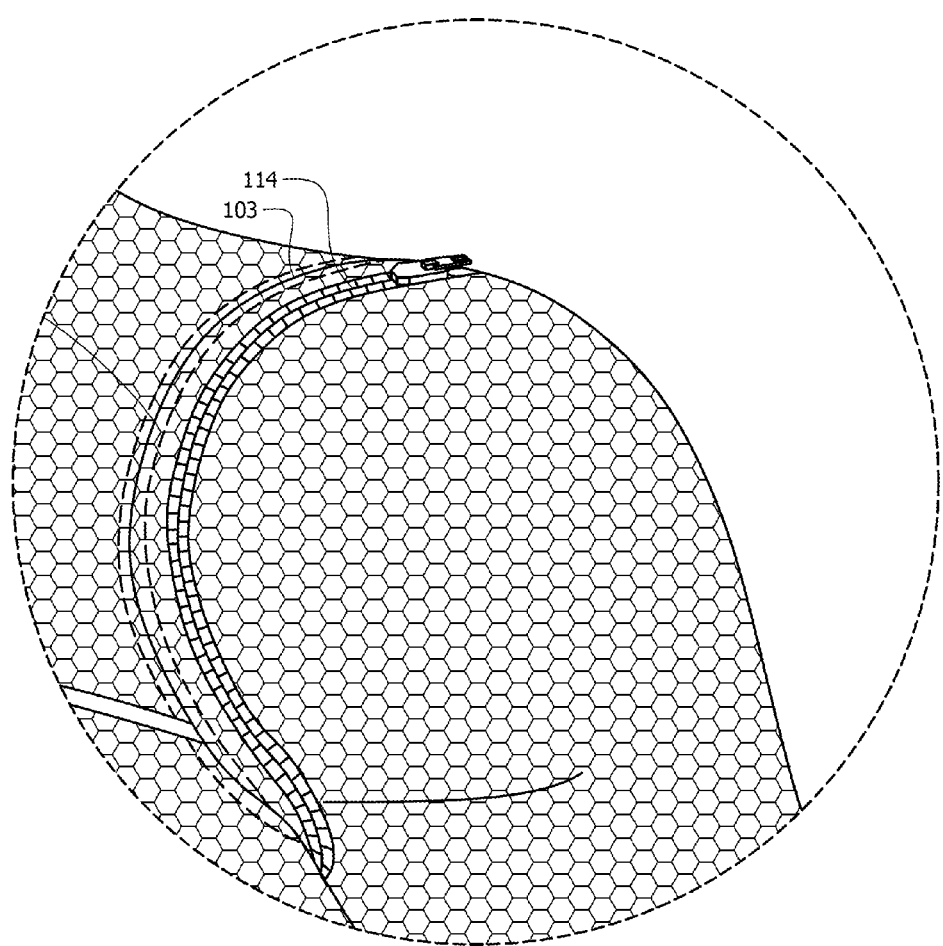
FIG. 13 is a close-up view of a shoulder section of the embodiment shown in FIG. 1.
Figure 14:
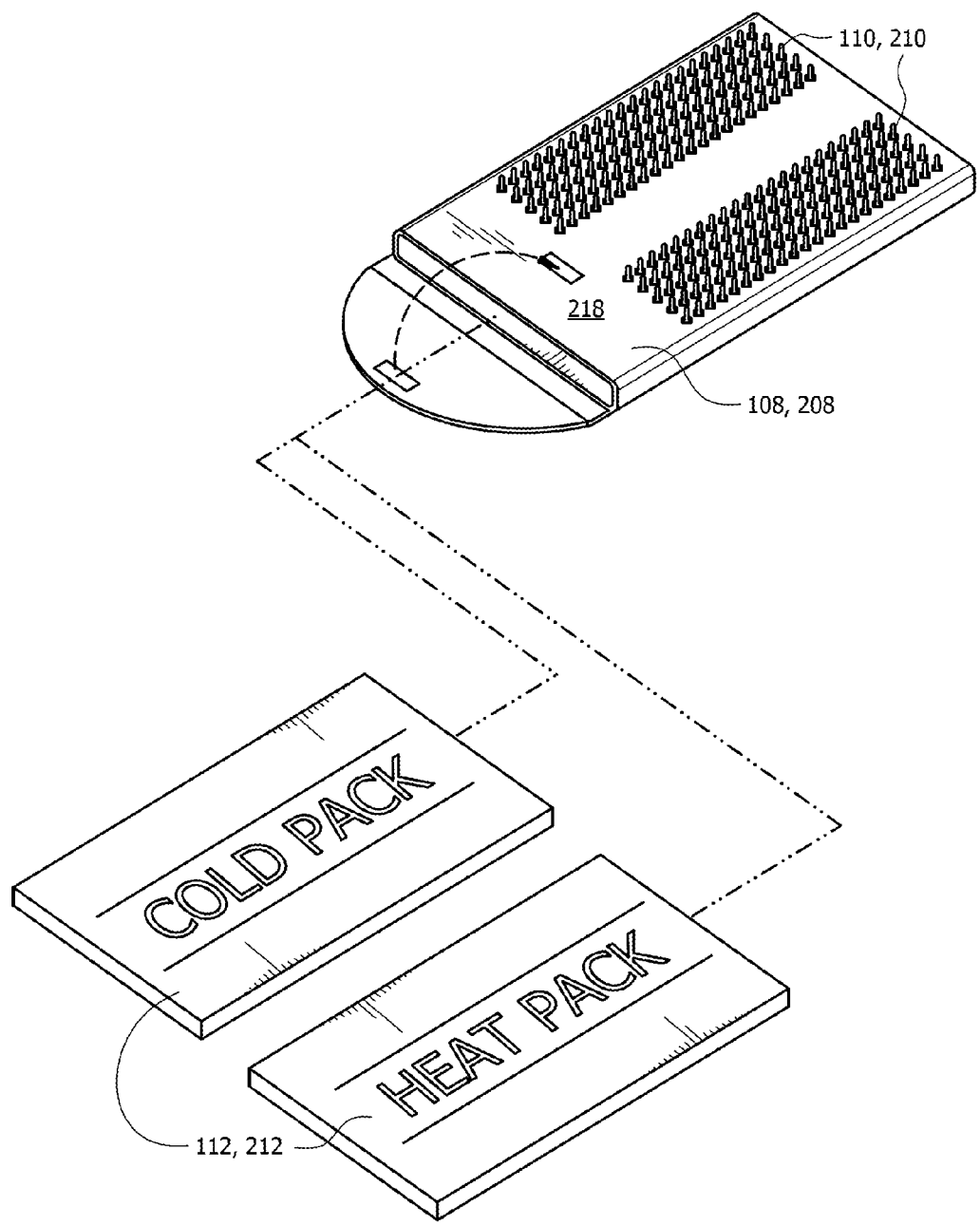
FIG. 14 is a certain embodiment of the thermal pouch having a closure mechanism.

FIGS. 10-12 provide additional embodiments 700, 800, and 900, respectively, illustrating sleeve-like designs to receive a user's limbs. The figures include outer mesh layer 704, 804, and 904, but show a cutaway in the outer mesh layer to highlight TFE 712, 812, and 912 in the intermediate space, respectively. The cutaway is provided solely for clarity purposes. Embodiments 700, 800, and 900 each have a single compartment of intermediate space, but certain embodiments may utilize multiple compartments for the sleeve-like designs. Additionally, the openings (not shown) are located in base layer 702, 802, and 902, but certain embodiments may utilize openings in the outer mesh layer. Furthermore, embodiments 700, 800, and 900 employ TFE 712, 812, and 912 which is similar to TFE 300 in FIG. 6, but the embodiments may utilize a thermal pouch and TFE similar to those shown in FIGS. 1-5.

All types of garments are considered including additional sleeve-like designs adaptive to receive certain body parts, especially limbs or joints. Especially considered garments include a shirt, jacket, or pants that may appear to others as a substantially normal garment. Athletic jackets, "sweats" and other sporting-related garments are especially contemplated, with the inner and outer layers comprising cotton, nylon, or other fabrics known to the industry, including performance fabrics. More specifically, and without limitation, the material can be moisture absorbent, breathable, stretchable, meshed, or any blend or combination thereof. Even more particularly, the material can be a blend of nylon, polyester, and spandex. The material can also be thermoconductive in order to better conduct heat between the TFE and the user's body, or thermoreflective to help keep heat inside the article of clothing.

In a certain embodiment, the garment may be substantially greater in size than the TFE. Such an embodiment would preferably have multiple connection points and openings between the inner and outer layers of the garment such that there exists multiple individual or independent compartments of intermediate space with each compartment having its own openings. Such a design eases the movement of the TFE to the desired treatment site by reducing the distance between the opening and the treatment site.

In a certain embodiment having multiple compartments of intermediate space, the compartments may have individuals shapes designed to mirror a musculoskeletal structure. As an example, if the garment was shirt-like, then such an embodiment may have individual compartments designed to treat each pectoral muscle, each shoulder, and the abdominal region. Additionally, the embodiment may have individual compartments to address the specific muscular structure of the back, such as individual compartments for the Trapezius, Rhomboid, Latissimus Dorsi, Erector Spinae, Teres Major and Teres Minor. Another example may be a sleeve designed to cover a user's knee, which could have a single compartment or multiple compartments designed to address the individual tendons in a knee joint. The individual compartments may vary in location and size to improve effectiveness of the present invention as known to a person having ordinary skill in the art.

In a certain embodiment, the present invention may include an additional third layer that encloses the inner base layer and outer mesh layer. The third layer may have one or more opening to allow the user access to the openings leading to the intermediate space. The third layer preferably provides thermal insulation to shield the TFE from the elements resulting in increased time before the temperature of the TFE reaches ambient temperature. In yet another embodiment, the present invention may not include the base layer such that the outer mesh layer holds the thermal pouch or TFE directly against a user's skin.

GLOSSARY OF CLAIM TERMS

Garment: is any form of clothing or apparel that is capable of covering all or a portion of one's body, including but not limited to joint sleeves and lumbar support braces Inward Facing: is a direction towards the base layer of the garment.

Mesh: is a material with generally evenly spaced holes.

Outward Facing: is a direction away from the base layer of the garment.

Thermal Transferring Element (TFE): is a packaged substance, such as a liquid or refrigerant gel, capable of being heated and/or cooled. The package may be permanently or temporarily sealed.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A garment for providing a wearer with compression and thermal therapy, comprising:
    a base layer and an outer layer, wherein the base layer is adapted to receive one or more body parts and abuts the skin of the wearer,
    the outer layer comprises mesh and is secured to the base layer such that an intermediate space is defined between the base layer and the outer layer, wherein the intermediate space is capable of receiving a thermal transferring element;
    an opening to the intermediate space through which the thermal transferring element can be removably inserted into the intermediate space;
    a thermal pouch capable of receiving the thermal transferring element, wherein the thermal pouch has an outward facing surface and an inward facing surface, the outward facing surface includes a plurality of generally linearly shaped projections that are generally equidistantly spaced and extend outwardly such that the plurality of projections are capable of being received by the holes in the mesh of the outer layer of the garment, the inward facing surface is thermally transmissive; and
    each projection having a base affixed to the outward facing surface and a tip protruding therefrom, whereby protrusion of the projections through the mesh holes cause the holes to circumscribe the individual projections between the base and the tip, which thereby provides resistance to lateral movement of the thermal transferring element.

2. The garment of claim 1, further comprising the thermal transferring element having a generally planar shape.

3. The garment of claim 1, further comprising the outer layer made of a flexible compressive material.

4. The garment of claim 1, further comprising the inward facing surface of the thermal pouch constructed of mesh with large holes to allow for increased thermal transfer.

5. The garment of claim 1, further comprising the outward facing surface of the thermal pouch constructed of a thermally insulating material.

6. The garment of claim 1, further comprising the thermal pouch including a closure mechanism.

7. The garment of claim 1, further comprising the opening to the intermediate space including a closure mechanism.

8. The garment of claim 1, further comprising the opening to the intermediate space located in the outer layer of the garment.

9. The garment of claim 1, further comprising the intermediate space compartmentalized into smaller compartments where each compartment includes an opening to allow the thermal pouch to be removably inserted into the compartments in the intermediate space.

10. A thermal transferring element, comprising:
    A substantially planar shape having a first side and a second side, where the first side is smooth and the second side contains a plurality of generally linearly shaped projections, the plurality of projections have a base affixed to the second side and a tip protruding therefrom, are generally equidistantly spaced and are adapted to be received by openings present in a mesh material, whereby the protrusion of the projections through the mesh openings cause the openings to circumscribe the individual projections between the base and the tip, which thereby provides resistance to lateral movement of the thermal transferring element.

11. The thermal transferring element of claim 10, further comprising the plurality of projections having individual projections being between about one millimeter and two millimeters in length.

12. The thermal transferring element of claim 10, further comprising the inward facing surface being more thermally transmissive than the outward facing surface.

13. A garment for providing a wearer with compression and thermal therapy, comprising:

a base layer and an outer layer, wherein the base layer is adapted to receive one or more body parts and abuts the skin of the wearer, the outer layer comprises mesh and is secured to the base layer such that an intermediate space is defined between the base layer and the outer layer, wherein the intermediate space is capable of receiving a thermal transferring element;

an opening to the intermediate space through which the thermal transferring element can be removably inserted into the intermediate space;

the thermal transferring element having a substantially planar shape including a first side and a second side, where the first side is smooth and the second side contains a plurality of projections, the plurality of generally linearly shaped projections are generally equidistantly spaced and extend outwardly such that the plurality of projections are capable of being received by the holes in the mesh of the outer layer of the garment; and each projection having a base affixed to the second surface and a tip protruding therefrom, whereby protrusion of the projections through the mesh holes cause the holes to circumscribe the individual projections between the base and the tip, which thereby provides resistance to lateral movement of the thermal transferring element.

14. The garment of claim 13, further comprising the base layer made of a flexible compressive material.

15. The garment of claim 13, further comprising the opening to the intermediate space including a closure mechanism.

16. The garment of claim 13, further comprising the opening to the intermediate space located in the base layer of the garment.

17. The garment of claim 13, further comprising the opening to the intermediate space located in the outer layer of the garment.

18. The garment of claim 13, further comprising the intermediate space compartmentalized into smaller compartments where each compartment includes an opening to allow the thermal transferring element to be removably inserted into the compartments in the intermediate space.

\* \* \* \* \*